(12) United States Patent
Kim et al.

(10) Patent No.: US 11,168,092 B2
(45) Date of Patent: Nov. 9, 2021

(54) COMPOUNDS AND METHOD OF PREVENTING OR TREATING CANCER USING THE SAME

(71) Applicant: Research & Business Foundation Sungkyunkwan University, Suwon-si (KR)

(72) Inventors: Ki Hyun Kim, Suwon-si (KR); Seungrak Lee, Cheongju-si (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 16/879,030

(22) Filed: May 20, 2020

(65) Prior Publication Data

US 2020/0377516 A1 Dec. 3, 2020

(30) Foreign Application Priority Data

May 30, 2019 (KR) .................... 10-2019-0063526
Oct. 24, 2019 (KR) .................... 10-2019-0132722

(51) Int. Cl.
*C07D 493/20* (2006.01)
*A61K 35/00* (2006.01)
*A23L 31/00* (2016.01)

(52) U.S. Cl.
CPC ............ *C07D 493/20* (2013.01); *A23L 31/00* (2016.08); *A61K 35/00* (2013.01)

(58) Field of Classification Search
CPC .................................................. C07D 493/20
See application file for complete search history.

(56) References Cited

PUBLICATIONS

Lee et al. (The 49th Annuyal Meeting and Syposiuum of the Korean Society of Pharmacognosy'2018).*
McMahon et al. (2000).*
Pinedo et al. (2000).*
Skeel, Roland T. et al., "Handbook of Cancer Chemotherapy", Wolters Kluwer Health, 2011, (pp. 1-200).
Lee, Seoung Rak et al., "Macrocyclic Trichothecene Mycotoxins from a Deadly Poisonous Mushroom, Podostroma cornu-damae", *The 49th Annual Meeting and Symposium of the Korean Society of Pharmacognosy*, Nov. 22-23, 2018 (pp. 1-5).
Lee, Seoung Rak et al., "Macrocyclic Trichothecene Mycotoxins from a Deadly Poisonous Mushroom, Podostroma cornu-damae", *Journal of Natural Products*, vol. 82, 2019(pp. 112-128).
Saikawa, Yoko, et al., "Toxic principles of a poisonous mushroom Podostroma cornu-damae." *Tetrahedron*, 57, 39, 2001 (pp. 8277-8281).
Li, Yong, et al., "Cytotoxic trichothecene-type sesquiterpenes from the sponge-derived fungus *Stachybotrys chartarum* with tyrosine kinase inhibition." *Rsc Advances*, 7, 12, 2017 (pp. 7259-7267).
Shen, Li, et al. "Cytotoxic trichothecene macrolides produced by the endophytic *Myrothecium roridum.*" *Journal of natural products*, 82, 6, 2019 (pp. 1503-1509).

* cited by examiner

*Primary Examiner* — Paul V Ward
(74) *Attorney, Agent, or Firm* — NSIP Law (57) ABSTRACT

The present disclosure relates to novel compounds and a method of preventing or treating cancer using the same, and more particularly to compounds having structural formulae 1 to 3. The compounds of the present disclosure exhibit an excellent activity of inhibiting various cancer cells, and thus can be effectively used in a composition or method for preventing, alleviating, or treating cancer.

7 Claims, 2 Drawing Sheets

| compound | IC$_{50}$ ($\mu$M)[a] | | | |
|---|---|---|---|---|
| | Bt549 | HCC70 | MDA-MB-231 | MDA-MB-468 |
| 1 | >10.0 | >10.0 | >10.0 | >10.0 |
| 2 | >10.0 | >10.0 | >10.0 | >10.0 |
| 3 | 1.8 | 7.7 | 3.6 | >10.0 |
| 4 | 0.00002 | 0.00002 | 0.00003 | 0.00005 |
| 5 | 1.8 | 2.2 | 2.0 | 3.4 |
| 6 | 0.0003 | 0.001 | 0.0004 | 0.003 |
| 7 | >10.0 | >10.0 | >10.0 | >10.0 |
| 8 | 0.004 | 0.02 | 0.02 | 0.08 |
| doxorubicin[b] | 0.01 | 0.05 | 0.08 | 0.07 |
| etoposide[b] | 1.8 | 1.8 | 2.3 | 2.1 |

COMPOUNDS AND METHOD OF PREVENTING OR TREATING CANCER USING THE SAME

CROSS-REFERENCE TO RELATED APPLICATION

This application claims priority to and the benefit of Korean Patent Application No. 2019-0063526, filed on May 30, 2019 and No. 2019-0132722 file on Oct. 24, 2019, the disclosure of which is incorporated herein by reference in its entirety.

BACKGROUND

1. Field

The present disclosure relates to novel compounds, a method of preventing or treating cancer using the same, and the like.

2. Discussion of Related Art

Cancer generally refers to a group of diseases that begin with uncontrollable cell proliferation, infiltrate into and destroy surrounding normal tissues or organs, and create new growth sites, thus taking an individual's life. In the past decade, despite remarkable progress in the control of cell cycle or apoptosis and the search for new targets, including oncogenic genes and cancer suppression genes, to conquer cancer, the incidence of cancer is increasing as civilization develops.

As a treatment method for cancer, chemotherapy, surgical therapy, and radiation therapy are used. Thereamong, chemotherapy is the most widely used for the treatment of cancer as a method using an anticancer agent. Today, about 60 different anticancer drugs are used in clinical trials, and new anticancer drugs are continuously being developed as knowledge about cancer development and characteristics of cancer cells is known. However, most of the anti-cancer drugs currently used in clinical trials are chemically synthesized substances, and in many cases, there may be side effects such as nausea, vomiting, ulcers in the oral cavity and small intestines, diarrhea, hair loss, and bone marrow suppression in which the production of active ingredients in blood is reduced. For example, mitomycin-C is known to have side effects such as renal failure, and adriamycin is known to have side effects such as bone marrow suppression. In particular, cisplatin, which is the most useful drug among anticancer drugs developed so far, is widely used in the treatment of testicular cancer, ovarian cancer, lung cancer, head and neck cancer, bladder cancer, stomach cancer, cervical cancer, and the like, but has a big problem with the occurrence of side effects, for example, hematopoietic toxicity such as anemia, digestive toxicity such as vomiting and nausea, kidney toxicity such as kidney tubular damage, difficulty in hearing, abnormalities in electrolytes in the body, shock, and peripheral nerve abnormalities.

Therefore, there is an urgent need to develop a novel anticancer agent which can solve the side effects and toxicity of conventional anticancer agents and has high safety.

SUMMARY

Accordingly, the inventors of the present disclosure discovered compounds that strongly inhibit the proliferation of cancer cells, and thus completed the present disclosure.

Therefore, provided is a compound having a Structural formula selected from the group consisting of the following structural formulae 1 to 3.

[Structural formula 1]

($R_1$ is one selected from the group consisting of OH, and $R_2$ is or

.)

[Structural formula 2]

($R_1$ and $R_2$ are each independently one selected from the group consisting of , and

)

[Structural formula 3]

Provided is a composition for preventing, alleviating, or treating cancer including, as an active ingredient, a compound having a Structural formula selected from the group consisting of structural formulae 1 to 3 or a pharmacologically acceptable salt thereof.

Provided is a method of preventing, alleviating, or treating cancer including administering, to an individual, a composition including, as an active ingredient, a compound having a structural formula selected from the group consisting of Structural formulae 1 to 3 or a pharmacologically acceptable salt thereof.

However, technical problems to be solved by the present disclosure are not limited to the above-described technical problems, and other unmentioned technical problems will become apparent from the following description to those of ordinary skill in the art.

To achieve the objective of the present disclosure, the inventors of the present disclosure discovered compounds that inhibit the proliferation of cancer cells, and thus completed the present disclosure.

According to an aspect of an embodiment, there is provided a compound having a structural formula selected from the group consisting of the following structural formulae 1 to 3.

[Structural formula 1]

($R_1$ is one selected from the group consisting of OH,

OH, and

5
-continued and or

)

[Structural formula 2]

($R_1$ and $R_2$ are each independently one selected from the group consisting of 6
-continued , and

,)

[Structural formula 3]

In one embodiment of the present disclosure, the compound may be isolated from *Podostroma cornu-damae* or a culture thereof.

Figure 1:
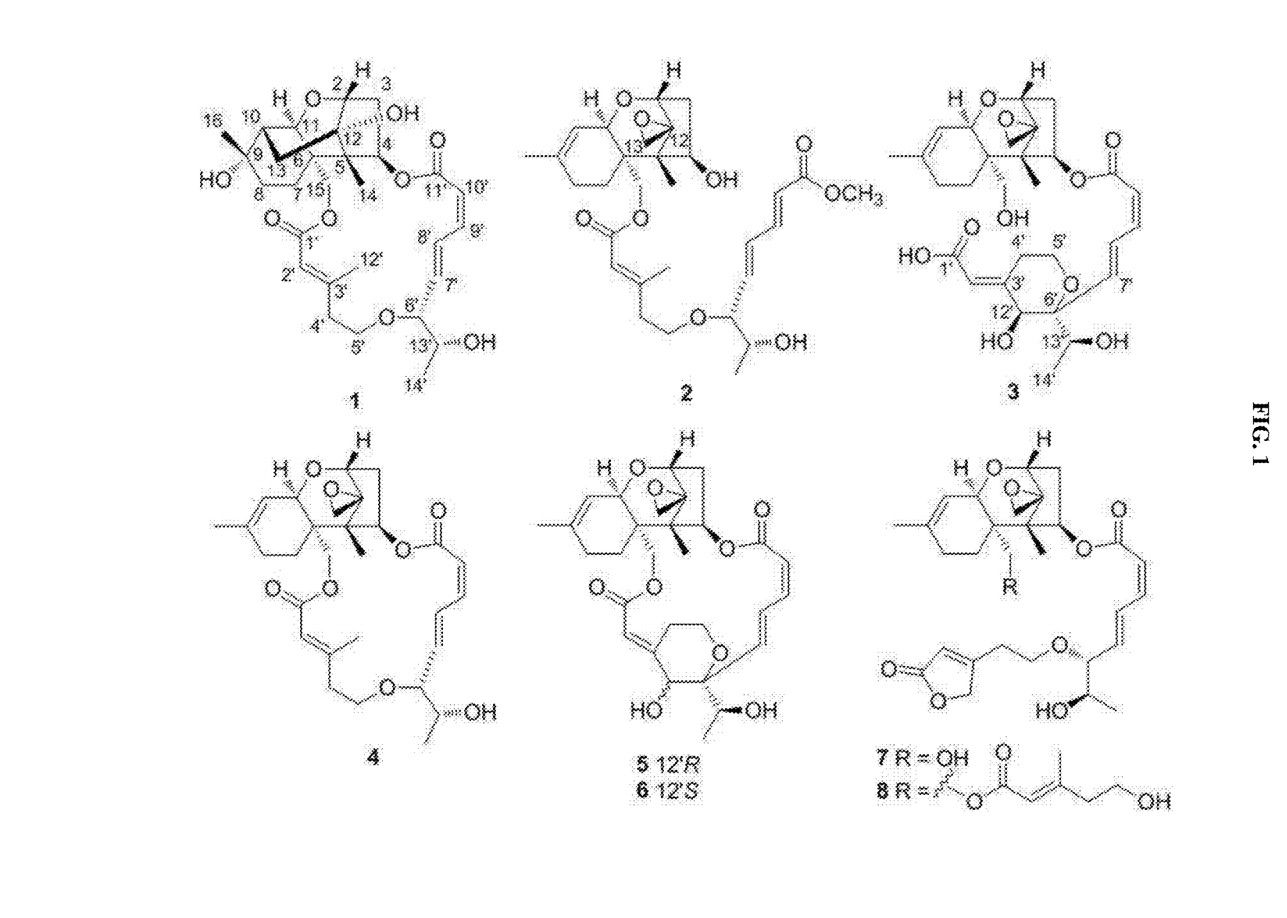
FIG. 1 illustrates structural Structural formulae of 8 compounds isolated and purified from *Podostroma cornu-damae* or a culture thereof.
Figure 2:
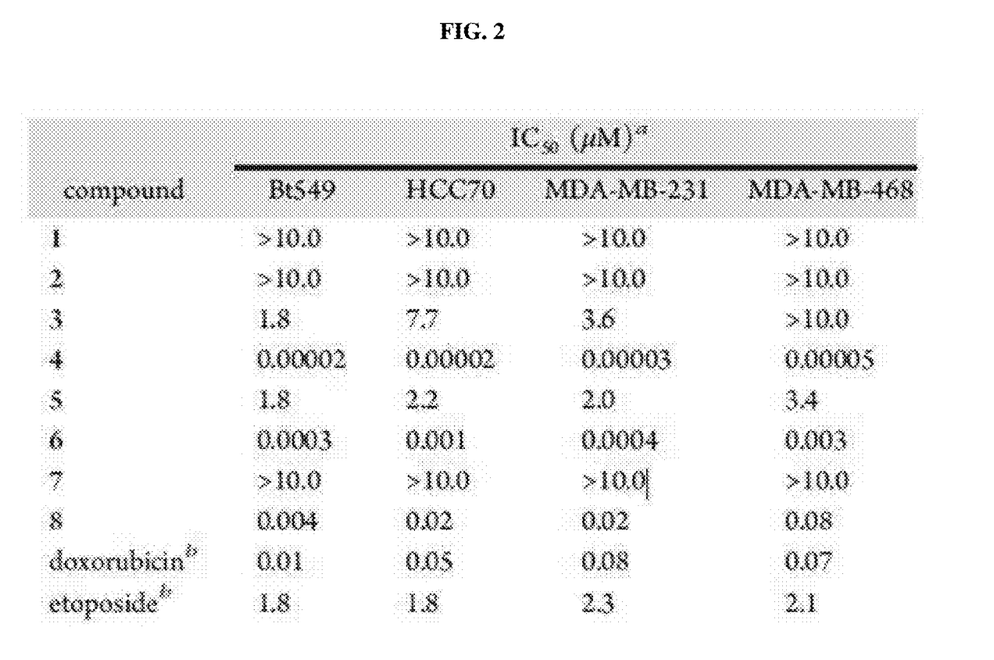
FIG. 2 illustrates, as $IC_{50}$ values, the degree of cytotoxicity effects of a total of 8 compounds (1-8) on 4 types of human breast cancer cells (Bt549, HCC70, MDA-MB-231, and MDA-MB-468).

In one embodiment of the present disclosure, the compound may include compounds 1 to 8. Compounds 1 to 8 are illustrated in FIG. 1.

According to an aspect of another embodiment, there is provided a method of preparing the compound, including: (a) extracting *Podostroma cornu-damae* with water or a $C_1$-$C_4$ organic solvent; (b) fractionating the extract obtained in process (a) with ethyl-acetate; and (c) separating and purifying, by concentration gradient chromatography, the ethyl acetate fraction obtained in process (b).

In one embodiment of the present disclosure, the organic solvent of process (a) may be selected from the group consisting of methanol, ethanol, propanol, isopropanol, butanol, acetone, ether, chloroform, ethyl acetate, methylene chloride, hexane, cyclohexane, dichloromethane, and petroleum ether.

According to an aspect of another embodiment, there is provided a composition for preventing, alleviating, or treating cancer including, as an active ingredient, a compound having a structural formula selected from the group consisting of structural formulae 1 to 3 or a pharmacologically acceptable salt thereof.

According to an aspect of another embodiment, there is provided a method of preventing, alleviating, or treating cancer, including administering, to an individual, a composition including, as an active ingredient, a compound having a Structural formula selected from the group consisting of structural formulae 1 to 3 or a pharmacologically acceptable salt thereof.

In one embodiment of the present disclosure, the composition may be a pharmaceutical composition or a food composition, but the present disclosure is not limited thereto.

In another embodiment of the present disclosure, the cancer may be one or more selected from the group consisting of cervical cancer, lung cancer, pancreatic cancer, non-small cell lung cancer, liver cancer, colon cancer, colorectal cancer, bone cancer, skin cancer, head cancer, neck cancer, skin melanoma, intraocular melanoma, uterine cancer, ovarian cancer, rectal cancer, brain tumors, bladder cancer, blood cancer, gastric cancer, anal cancer, breast cancer, fallopian tube carcinoma, endometrial carcinoma, vaginal cancer, vulva carcinoma, Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, kidney cancer, urinary tract cancer, renal cell carcinoma, renal pelvis carcinoma, central nervous system (CNS) tumors, primary CNS lymphoma, spinal cord tumors, brainstem glioma, and pituitary adenoma, but the present disclosure is not limited thereto.

According to an aspect of another embodiment, there is provided a use of the compound for preventing, alleviating, or treating cancer.

According to an aspect of another embodiment, there is provided a use of the compound for preparing a drug for the prevention, alleviation, or treatment of cancer.

BRIEF DESCRIPTION OF THE DRAWINGS

The above and other objects, features and advantages of the present disclosure will become more apparent to those of ordinary skill in the art by describing in detail exemplary embodiments thereof with reference to the accompanying drawings, in which.

DETAILED DESCRIPTION OF EXEMPLARY EMBODIMENTS

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects.

To achieve the objective of the present disclosure, the inventors of the present disclosure discovered compounds having an excellent effect of inhibiting the proliferation of cancer cells, and thus completed the present disclosure.

Therefore, the present disclosure provides a compound having a structural formula selected from the group consisting of the following structural formulae 1 to 3.

[Structural formula 1]

$R_1$ is one selected from the group consisting of OH, and $R_2$ is or

.)

[Structural formula 2]

($R_1$ and $R_2$ are each independently one selected from the group consisting of , and

,)

[Structural formula 3]

The compound having a structural formula selected from the group consisting of Structural formulae 1 to 3 is first verified by the inventors of the present disclosure, and is well shown in the specification examples of the present disclosure.

The compound may be, more particularly, compounds 1 to 8 as illustrated in FIG. 1, but the present disclosure is not limited thereto.

The IUPAC names of compounds 1 to 8 illustrated in FIG. 1 are as follows:

TABLE 1

| Compound | IUPAC name |
| --- | --- |
| 1 | (1R,4Z,6E,8R,12E,16aR,19S,20S,20aR,22R,23S,23aS)-19,23-dihydroxy-8-((R)-1-hydroxyethyl)-12,19,23a-trimethyl-10,11,17,18,19,20,20a,22,23,23a-decahydro-1H-1,22:20,23-dimethano[1,6,12]trioxacyclo-octadecino[3,4-d]chromene-3,14(8H,16H)-dione |
| 2 | (2E,4E,6R,7R)-methyl-7-hydroxy-6-(((E)-5-(((2R,2'S,4R,5S,5aR,9aR)-4-hydroxy-5,8-dimethyl-2,3,4,5,5a,6,7,9a-octahydrospiro[2,5-methanobenzo[b]oxepine-10,2'-oxiran]-5a-yl)methoxy)octa-2,4-dienoate |
| 3 | (E)-2-((3S)-3-hydroxy-2-((S)-1-hydroxyethyl)-2-((1E,3Z)-5-(((2R,2'S,4R,5S,5aR,9aR)-5a-(hydroxymethyl)-5,8-dimethyl-2,3,4,5,5a,6,7,9a-octahydrospiro[2,5-methanobenzo[b]oxepine-10,2'-oxiran]-4-yl)oxy)-5-oxopenta-1,3-dien-1-yl)dihydro-2H-pyran-4(3H)-ylidene)acetic acid |
| 4 | (1R,2'S,4Z,6E,8R,12E,16aR,20aR,22R,23aS)-8-((R)-1-hydroxyethyl)-12,19,23a-trimethyl-1,10,11,17,18,20a,22,23a-octahydrospiro[1,22-methano[1,6,12]trioxacyclooctadecino[3,4-d]chromene-23,2'-oxirane]-3,14(8H,16H)-dione |
| 5 | (2'S,4E,9R,10E,12Z,16R,16aS,18R,19aR,23aR,25R)-6,7,16,16a,19a,22-Hexahydro-25-hydroxy-9-[(1S)-1-hydroxyethyl]-16a,21-dimethylspiro[5,9:16,18-dimethano-1H,3H,23H-[1,6,12]trioxacyclo-octadecino[3,4-d][1]benzopyran-17(18H),2'-oxirane]-3,14(9H)-dione |
| 6 | Epi-(2'S,4E,9R,10E,12Z,16R,16aS,18R,19aR,23aR,25R)-6,7,16,16a,19a,22-Hexahydro-25-hydroxy-9-[(1S)-1-hydroxyethyl]-16a,21-dimethylspiro[5,9:16,18-dimethano-1H,3H,23H-[1,6,12]trioxacyclooctadecino[3,4-d][1]benzopyran-17(18H),2'-oxirane]- 3,14(9H)-dione |
| 7 | (2Z,4E)-(2R,2'S,4R,5S,5aR,9aR)-5a-(hydroxymethyl)-5,8-dimethyl-2,3,4,5,5a,6,7,9a-octahydrospiro[2,5-methanobenzo[b]oxepine-10,2'-oxiran]-4-yl 7-hydroxy-6-(2-(5-oxo-2,5-dihydrofuran-3-yl)ethoxy)octa-2,4-dienoate |

TABLE 1-continued

| Compound | IUPAC name |
| --- | --- |
| 8 | (2Z,4E)-(2R,2'S,4R,5S,5aR,9aR)-5a-((((E)-5-hydroxy-3-methylpent-2-enoyl)oxy)methyl)-5,8-dimethyl-2,3,4,5,5a,6,7,9a-octahydrospiro[2,5-methanobenzo[b]oxepine-10,2'-oxiran]-4-yl-7-hydroxy-6-(2-(5-oxo-2,5-dihydrofuran-3-yl)ethoxy)octa-2,4-dienoate |

The compounds may have a non-aromatic double bond and one or more asymmetric centers. Thus, they may occur as racemates and racemic mixtures, single enantiomers, individual diastereomers, diastereomeric mixtures, and cis- or trans-isomers. These isomer forms are all considered.

In addition, the present disclosure may include a derivative compound such as a hydrate of a compound having a structural formula selected from the group consisting of structural formulae 1 to 3 or a glycoside in which a compound such as glucose is bound to each side chain.

The compounds according to the present disclosure may be isolated from nature or may be prepared by chemical synthesis of compounds known in the art.

Preferably, the compound of the present disclosure may be isolated and purified from natural plants. That is, they may be obtained from plants or parts thereof using an existing method of extracting and separating materials. To obtain a desired extract, stems, roots, or leaves may be appropriately dried and macerated or may be simply dried and extracted with an appropriate organic solvent, and the desired extract may be purified using a purification method known in the art to which the present disclosure pertains. Preferably, the compound of the present disclosure may be isolated and purified from *Podostroma cornu-damae* or a culture thereof.

As used herein, the term "*Podostroma cornu-damae*" refers to a species of poisonous mushrooms belonging to the order Hypocreales and the family Hypocreaceae. The poison is a trichothecene type of poison. A fruiting body has a cylindrical form with a size of 1-8×0.7-1.4 cm, but is branched to form an antler form or a stalagmite form. In the fruiting body, the surface has a reddish-orange color, the inside is white, and the perithecium is buried in an outer layer of the upper surface. The *Podostroma cornu-damae* of the present disclosure is a scientific name. These plants are distributed worldwide and may be found in, particularly, Korea and Japan.

As used herein, the term "culture" encompasses a culture medium itself obtained by culturing *Podostroma cornu-damae* according to the present disclosure in a suitable liquid medium, a filtrate obtained by filtering or centrifuging the culture medium to remove the strain (filtrate or centrifuged supernatant), a cell lysate obtained by ultrasonically treating the culture medium or treating the culture medium with lysozyme, and the like, preferably a supernatant after centrifugation, but the present disclosure is not limited thereto. In addition, the culture medium may include both a concentrate of the culture medium and a dried product of the culture medium.

The compound of the present disclosure may be isolated and purified using a method including the following processes:

(a) extracting *Podostroma cornu-damae* with water or a $C_1$-$C_4$ organic solvent;

(b) fractionating the extract obtained in process (a) with ethyl acetate; and (c) separating and purifying, by concentration gradient chromatography, the ethyl acetate fraction obtained in process (b).

In process (a), the whole or a dried body of *Podostroma cornu-damae* may be used, and the dried body may be used after being pulverized using a pulverizer, to enhance extraction efficiency. As a drying method, sun drying, shade drying, hot air drying, freeze drying, and natural drying may be used.

The $C_1$-$C_4$ organic solvent used in the extraction may be methanol, ethanol, propanol, isopropanol, butanol, acetone, ether, chloroform, ethyl acetate, methylene chloride, hexane, cyclohexane, dichloromethane, or petroleum ether. In one embodiment of the present disclosure, *Podostroma cornu-damae* was extracted with methanol.

In process (b), the extract obtained in process (a) is fractionated using ethyl acetate, for distribution extraction. The ethyl acetate fraction obtained in process (b) is separated by concentration gradient chromatography. As the chromatography, a column packed with various synthetic resins such as silica gel or activated alumina (column chromatography), high-speed liquid chromatography (HPLC), and the like may be used alone or in combination. Preferably, among the fractions obtained in process (b), the ethyl acetate fraction may be applied to a silica gel column, and while gradually increasing polarity by adjusting the composition of an elution solvent, various fractions may be obtained. Among the fractions obtained in the above-described process, a fraction with activity may be again subjected to concentration gradient silica gel chromatography by gradually increasing polarity by adjusting the composition of an elution solvent. However, the method for extraction and separation and purification of the compound is not necessarily limited to the above-described method.

Process (c) is a process of separating and purifying, by concentration gradient chromatography, the ethyl acetate fraction obtained in process (b).

As the chromatography, a column packed with various synthetic resins such as silica gel or activated alumina (column chromatography), high-speed liquid chromatography (HPLC), and the like may be used alone or in combination. Preferably, the compound may be separated and purified by HPLC.

The present disclosure also provides a composition for preventing, alleviating, or treating cancer including, as an active ingredient, a compound having a structural formula selected from the group consisting of structural formulae 1 to 3 or a pharmacologically acceptable salt thereof.

The compound having a Structural formula selected from the group consisting of Structural formulae 1 to 3 is the same as described above.

The compound of the present disclosure may be isolated and purified from *Podostroma cornu-damae*, or may be prepared using a chemical synthesis method known in the art. For example, the compound of the present disclosure and derivatives thereof may be extracted from *Podostroma cornu-damae*. The compound may be extracted using a known method commonly used in the art, such as organic solvent extraction and chromatography.

The compound according to the present disclosure may be used as is or in the form of a pharmaceutically acceptable salt thereof. As used herein, the term "pharmaceutically acceptable" refers to a non-toxic composition that is physiologically acceptable and does not generally cause an allergic reaction or similar reaction when administered to a human, and the salt may be an acid addition salt formed by a pharmaceutically acceptable free acid. As the free acid, an organic acid and an inorganic acid may be used. The organic acid includes, but is not limited to, citric acid, acetic acid, lactic acid, tartaric acid, maleic acid, fumaric acid, formic acid, propionic acid, oxalic acid, trifluoroacetic acid, benzoic acid, gluconic acid, meta-sulfonic acid, glycolic acid, succinic acid, 4-toluenesulfonic acid, glutamic acid, and aspartic acid. In addition, the inorganic acid includes, but is not limited to, hydrochloric acid, bromic acid, sulfuric acid, and phosphoric acid.

The term "cancer" as used herein refers to a disease related to cell death regulation, and a disease caused by overproliferation of cells when the balance of normal apoptosis is broken. These abnormal hyperproliferative cells may invade surrounding tissues and organs in some cases to form masses and may cause the destruction or deformation of a normal structure in the body, which is collectively referred to as cancer.

Generally, a tumor refers to a mass that is abnormally grown by autonomous overgrowth of body tissue, and the tumor can be divided into a benign tumor and a malignant tumor. Malignant tumors have a very rapid growth rate compared to benign tumors, and metastasis occurs when they infiltrate surrounding tissues, which is life-threatening. These malignant tumors are commonly referred to as "cancer."

In the present disclosure, the type of cancer is not particularly limited. Non-limiting examples of the cancer may include cervical cancer, lung cancer, pancreatic cancer, non-small cell lung cancer, liver cancer, colon cancer, colorectal cancer, bone cancer, skin cancer, head cancer, neck cancer, skin melanoma, intraocular melanoma, uterine cancer, ovarian cancer, rectal cancer, brain tumors, bladder cancer, blood cancer, gastric cancer, anal cancer, breast cancer, fallopian tube carcinoma, endometrial carcinoma, vaginal cancer, vulva carcinoma, Hodgkin's disease, esophageal cancer, small intestine cancer, endocrine gland cancer, thyroid cancer, parathyroid cancer, adrenal cancer, soft tissue sarcoma, urethral cancer, penile cancer, prostate cancer, kidney cancer, urinary tract cancer, renal cell carcinoma, renal pelvis carcinoma, central nervous system (CNS) tumors, primary CNS lymphoma, spinal cord tumors, brainstem glioma, and pituitary adenoma, but the present disclosure is not limited thereto.

The amount of the composition according to the present disclosure is not particularly limited depending on the purpose of use or applications, and may range from, for example, about 0.001 wt % to about 99 wt %, preferably about 0.5 wt % to about 50 wt %, and more preferably, about 1 wt % to about 30 wt %, with respect to the total weight of the composition. In addition, the pharmaceutical composition according to the present disclosure may further include an additive such as a pharmaceutically acceptable carrier, excipient or diluent, in addition to the active ingredient.

The pharmaceutical composition according to the present disclosure may contain the compound alone or may be formulated in a suitable form with a pharmaceutically acceptable carrier.

The pharmaceutically acceptable carrier is commonly used in formulation, and includes, but is not limited to, saline, sterile water, Ringer's solution, buffered saline, cyclodextrin, a dextrose solution, a maltodextrin solution, glycerol, ethanol, and liposomes, and as necessary, may further include other general additives such as an antioxidant and a buffer. In addition, the composition may be formulated into an injectable preparation such as an aqueous solution, a suspension, or an emulsion, pills, capsules, granules, or tablets by additionally adding a diluent, a dispersant, a surfactant, a binder, a lubricant, and the like. For suitable pharmaceutically acceptable carriers and formulations, Structural formulations are preferably performed according to each ingredient using methods disclosed in Remington's documents. The pharmaceutical composition of the present disclosure is not particularly limited in terms of formulations, but may be Structural formulated into an injection, an inhalant, a dermatologic agent, or an oral ingestible agent.

The pharmaceutically acceptable carrier may include, for example, a carrier for oral administration or a carrier for parenteral administration. The carrier for oral administration may include lactose, starch, cellulose derivatives, magnesium stearate, stearic acid, and the like. In addition, the carrier for oral administration may include various drug delivery materials used for oral administration. In addition, the carrier for parenteral administration may include water, a suitable oil, saline, aqueous glucose, glycol, and the like, and may further include a stabilizer and a preservative. Suitable stabilizers include antioxidants such as sodium hydrogen sulfite, sodium sulfite, and ascorbic acid. Suitable preservatives include benzalkonium chloride, methyl- or propyl-parabens, and chlorobutanol. The pharmaceutical composition of the present disclosure may further include a lubricant, a wetting agent, a sweetener, a flavoring agent, an emulsifying agent, a suspending agent, and the like, in addition to the above-listed ingredients. For other pharmaceutically acceptable carriers and preparations, refer to those described in the following document (Remington's Pharmaceutical Sciences, 19th ed., Mack Publishing Company, Easton, Pa., 1995).

As used herein, the term "administration" means providing an individual with a predetermined composition of the present disclosure in any suitable way.

The composition of the present disclosure may be administered in any way to mammals, including humans. For example, the composition may be administered orally or parenterally. The parenteral administration may be, but is not limited to, intravenous administration, intramuscular administration, intraarterial administration, intramedullary administration, intrathecal administration, intracardiac administration, transdermal administration, subcutaneous administration, intraperitoneal administration, intranasal administration, intestinal administration, topical administration, sublingual administration, or rectal administration.

The pharmaceutical composition of the present disclosure may be formulated as a formulation for oral administration or parenteral administration according to the administration route as described above.

In the case of preparations for oral administration, the composition of the present disclosure may be formulated, using methods known in the art, into powders, granules, tablets, pills, sugar-coated tablets, capsules, liquids, gels, syrups, slurries, suspensions, and the like. For example, oral preparations may be obtained as tablets or sugar-coated tablets by blending the active ingredient with a solid excipient, pulverizing the same, adding a suitable adjuvant thereto, and then processing the resulting mixture into a granule mixture. Non-limiting examples of suitable excipients include sugars including lactose, dextrose, sucrose, sorbitol, mannitol, xylitol, erythritol, and maltitol, starches including corn starch, wheat starch, rice starch, and potato starch, celluloses including cellulose, methyl cellulose, sodium carboxymethyl cellulose, and hydroxypropyl methyl-cellulose, and fillers such as gelatin and polyvinylpyrrolidone. In addition, as necessary, the composition may include a disintegrant such as cross-linked polyvinylpyrrolidone, agar, alginic acid, or sodium alginate. Furthermore, the pharmaceutical composition of the present disclosure may further include an anti-coagulant, a lubricant, a wetting agent, a flavor, an emulsifying agent, and a preservative.

In the case of preparations for parenteral administration, the composition may be formulated, using methods known in the art, in the form of an injection, a cream, a lotion, an ointment for external application, oil, a moisturizer, a gel, an aerosol, and a nasal inhalant. The pharmaceutical composition of the present disclosure may be formulated according to methods known in the art along with a suitable parenteral carrier. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate. For other pharmaceutically acceptable carriers, refer to those described in the following document (Remington's Pharmaceutical Sciences, 19th ed., 1995, Mack Publishing Company, Easton, Pa.).

The composition according to the present disclosure is administered in a pharmaceutically effective amount. The term "pharmaceutically effective amount" as used herein refers to an amount sufficient to treat diseases at a reasonable benefit/risk ratio applicable to medical treatment, and an effective dosage level may be determined according to factors including type of diseases of patients, the severity of disease, the activity of drugs, sensitivity to drugs, administration time, administration routes, excretion rate, treatment periods, and simultaneously used drugs, and other factors well known in the medical field. The composition according to the present disclosure may be administered alone or in combination with other therapeutic agents and may be administered sequentially or simultaneously with existing therapeutic agents, and may be administered in a single dose or multiple doses. It is important to administer the composition in the minimum amount that enables achievement of the maximum effects without side effects in consideration of all the above-described factors, and this may be easily determined by those of ordinary skill in the art.

In particular, the effective amount of the composition according to the present disclosure may vary according to the age, gender, and body weight of a patient, may generally range from about 0.0001 mg/kg (body weight) to about 150 mg/kg, preferably about 0.001 mg/kg to about 100 mg/kg, and the composition may be administered daily or every other day or once to three times a day. However, the dosage may be increased or decreased according to administration route, the severity of obesity, gender, body weight, age, and the like, and thus the dosage is not intended to limit the scope of the present disclosure in any way.

Furthermore, the pharmaceutical composition of the present disclosure may be administered in combination with a known compound having an effect of preventing or treating cancer.

A food composition of the present disclosure includes all forms such as a functional food, a nutritional supplement, a health food, and food additives.

The food composition includes a health functional food composition.

These types of food compositions may be prepared in various forms according to general methods known in the art.

In the health functional food composition of the present disclosure, the active ingredient may be added to a food as is or may be used in combination with other foods or food ingredients, and may be appropriately used according to a general method. The amount of the active ingredient to be mixed may be appropriately determined according to the purpose of use (for prevention or alleviation). Generally, when preparing a food or a beverage, the composition of the present disclosure is added in an amount of 15 wt % or less, preferably 10 wt % or less, with respect to the total amount of raw materials. However, in the case of long-term ingestion for health and hygienic purposes or for health control purposes, the amount may be below the above range.

The health functional food composition of the present disclosure may include the active ingredient as an essential ingredient at the indicated proportion, and there are no particular limitations on the other ingredients, and the health functional food composition may include additional ingredients such as various flavoring agents, natural carbohydrates, or the like as in general beverages. Examples of the above-described natural carbohydrates include general sugars such as monosaccharides, e.g., glucose and fructose; disaccharides, e.g., maltose and sucrose; and polysaccharides such as dextrin and cyclodextrin, and sugar alcohols such as xylitol, sorbitol, and erythritol. As a flavoring agent other than the above-described flavoring agents, a natural flavoring agent (thaumatin and *stevia* extracts (e.g., rebaudioside A, glycyrrhizin, and the like) and a synthetic flavoring agent (saccharin, aspartame, and the like) may be used. The proportion of the natural carbohydrates may be appropriately selected and determined by those of ordinary skill in the art.

In addition to the above-listed ingredients, the health functional food composition of the present disclosure may include various nutritional supplements, vitamins, minerals (electrolytes), flavors such as synthetic flavors and natural flavors, colorants and enhancers (cheese, chocolate, and the like), pectic acid and salts thereof, alginic acid and salts thereof, organic acids, a protective colloid thickener, a pH adjuster, a stabilizer, a preservative, glycerin, alcohols, a carbonating agent used in carbonated beverages, and the like. These ingredients may be used alone or a combination thereof may be used. The proportion of these additive may also be appropriately selected by those of ordinary skill in the art.

In addition, a functional food may be prepared by adding the compound of the present disclosure or a derivative or pharmaceutically acceptable salt thereof to beverages (including alcoholic beverages), fruits and processed foods thereof (e.g., canned fruits, bottled foods, jam, and marmalade), fish, meat and processed foods thereof (e.g., ham, sausage, corn, and beef), bread and noodles (e.g., Japanese-style noodles, buckwheat noodles, ramen, spaghetti, and macaroni), fruit juices, various drinks, cookies, taffy, dairy products (e.g., butter and cheese), edible vegetable oils, margarine, vegetable proteins, retort foods, frozen foods, various seasonings (e.g., soybean paste, soy sauce and other sauces), or the like.

A suitable amount of the compound in the food composition of the present disclosure is not limited thereto, but may range from, for example, about 0.0001 wt % to about 30 wt % with respect to a finally produced food. Preferably, the compound may be included in the finally produced food in an amount of about 0.001 wt % to about 20 wt %.

In addition, in order to use the compound of the present disclosure in the form of a food additive, it may be prepared and used in the form of powder or a concentrate.

The present disclosure also provides a method of preventing, alleviating, or treating cancer, including administering, to an individual, a composition including, as an active ingredient, a compound having a structural formula selected from the group consisting of structural formulae 1 to 3 or a pharmacologically acceptable salt thereof.

The present disclosure also provides a use of a pharmaceutical composition including, as an active ingredient, the compound having a structural formula selected from the group consisting of structural formulae 1 to 3 for preventing, alleviating, or treating cancer.

The present disclosure also provides a use of the compound having a structural formula selected from the group consisting of structural formulae 1 to 3 for preparing a drug used for cancer treatment.

As used herein, the term "individual" refers to a subject to which the composition of the present disclosure may be administered, and the subject is not limited. The subject of the present disclosure may be preferably a mammal including a human, for example, a mammal such as a human, mouse, rat, monkey, cat, dog, cow, or pig, but the present disclosure is not limited thereto.

The term "prevention" as used herein means all actions that inhibit or delay the onset of diseases, the term "treatment" as used herein means all actions that alleviate or beneficially change a target disease and metabolic disorders according thereto via administration of the pharmaceutical composition according to the present disclosure, and the term "alleviation" as used herein means all actions that decrease the degree of parameters related to target diseases, e.g., symptoms.

Hereinafter, exemplary embodiments will be described to aid in understanding of the present disclosure. However, the following examples are provided only to facilitate the understanding of the present disclosure and are not intended to limit the scope of the present disclosure.

Experimental Example 1: Isolation of Trichothecene Compound from *Podostroma cornu-damae*

0.5 g of dried *Podostroma cornu-damae* fruiting bodies were secured and cultured on 50 potato dextrose agars (PDAs) at 25° C. for one month. After the culture was completed, PDAs were finely chopped and extracted a total of three times with 90% methanol, and filtered via a filter and concentrated, thereby obtaining a total of 12 g of a methanol crude extract. The obtained crude extract was dissolved in 700 mL of tertiary distilled water, followed by solvent fractionation with 700 mL of ethyl acetate, and the ethyl acetate fraction was concentrated to thereby obtain 400 mg of a fraction. The ethyl acetate fraction was subjected to high-performance liquid chromatography (HPLC) using acetonitrile and tertiary distilled water to obtain a total of six subfractions (A-F). 20 mg of subfraction C was subjected to HPLC using methanol and tertiary distilled water to obtain compounds 1 and 3 in amounts of 3.4 mg and 5.0 mg, respectively. 30 mg of subfraction D was subjected to HPLC using methanol and tertiary distilled water to obtain compounds 2, 5, 7, and 8 in amounts of 3.7 mg, 2.7 mg, 3.5 mg, and 4.3 mg, respectively. 25 mg of subfraction E was subjected to HPLC using methanol and tertiary distilled water to obtain 5.5 mg of compound 6. 26 mg of subfraction E was subjected to HPLC using methanol and tertiary distilled water to obtain 6.0 mg of compound 4. The trichothecene compounds may be represented by Structural formula 1, and specific names thereof are miophytocen D (1), roridin F (2), satratoxin I (3), roridin E (4), satratoxin H (5), 12'-episatratoxin H (6), roridin L-2 (7), and trichoverritone (8), respectively (see FIG. 1).

Experimental Example 2: Evaluation of Anticancer Activity of Trichothecene Compounds To confirm the cytotoxicity of the trichothecene compounds on four types of human breast cancer cells ((Bt549, HCC70, MDA-MB-231, and MDA-MB-468), lung cancer cells (A549), ovarian cancer cells (SK-OV-3), skin cancer cells (SK-MEL-2), and colorectal cancer cells (HCT15), sulforhodamine B (SRB) bioassay was performed. Respective cancer cells were exposed to each compound for 72 hours, and then the culture medium was removed, followed by fixation with trichloroacetic acid at 4° C. for 1 hour. After washing with water, respective cancer cells were stained with 0.4% SRB at 25° C. for 30 minutes and immersed in a 10 mM Tris base solution, and then absorbance at 520 nm was observed. Thereafter, the degree to which the growth of cancer cells was inhibited was determined as $IC_{50}$ values.

Example 1: Anticancer Activity of Trichothecene Compounds Against Breast Cancer Cells It was determined whether the compounds obtained from *Podostroma cornu-damae* and a culture thereof exhibit cytotoxicity against the four types of breast cancer cells (Bt549, HCC70, MDA-MB-231, and MDA-MB-468). To this end, doxorubicin and etoposide, which are representative anticancer drugs used in clinical trials, were used as positive controls.

As a result, as illustrated in FIG. 2, it was confirmed that compounds 4, 6, and 8 exhibited an $IC_{50}$ value ranging from 0.02 nM to 80 nM, indicating much higher activity than doxorubicin as a positive control, and it was found that compounds 3 and 5 exhibited an $IC_{50}$ value ranging from 1.8 μM to 7.7 μM, which were comparable to that of etoposide. From the above-described results, it was confirmed that some structural modifications to the trichothecene compounds provided very significant information on the structure-activity relationship for developing new anticancer drugs.

Example 2: Confirmation of Anticancer Activity of Trichothecene Compounds Against Cancer Cells The cytotoxicity of each of compounds 1 to 8 against lung cancer cells (A549), ovarian cancer cells (SK-OV-3), skin cancer cells (SK-MEL-2), and colorectal cancer cells (HCT15) was examined.

The results thereof are shown in Table 2 to 9.

Compound 4 exhibited an $IC_{50}$ value of less than 0.0001 μM for all of lung cancer, ovarian cancer, skin cancer, and colorectal cancer, from which it was confirmed that the anticancer activity thereof was very high.

It was also confirmed that compound 8 exhibited an $IC_{50}$ value of less than 0.07 μM, showing very high anticancer activity, and compound 6 exhibited an $IC_{50}$ value of less than 0.003 μM, showing very high anticancer activity.

It was also confirmed that compound 5 exhibited an $IC_{50}$ value ranging from 1.93 μM to 4.22 μM, showing high cancer cell inhibitory activity.

It was confirmed that compound 3 exhibited $IC_{50}$ values of 4.52 μM and 3.74 μM, respectively, for ovarian cancer and colorectal cancer, showing a strong anticancer effect.

TABLE 2

Anticancer activity of compound 1

| Concentration (mM) | Cell | | | |
|---|---|---|---|---|
| | A549 | SK-OV-3 | SK-MEL-2 | HCT15 |
| 0.0001 | 93.03 | 98.54 | 95.73 | 101.55 |
| 0.001 | 94.31 | 100.24 | 101.17 | 101.52 |
| 0.01 | 92.44 | 89.90 | 96.51 | 102.70 |
| 0.1 | 95.94 | 95.08 | 96.60 | 101.58 |
| 1.0 | 97.91 | 103.77 | 96.98 | 103.41 |
| 10.0 | 93.12 | 87.76 | 91.60 | 91.11 |
| $IC_{50}$ | >10.0 | >10.0 | >10.0 | >10.0 |

TABLE 3

Anticancer activity of compound 2

| Concentration (mM) | Cell | | | |
|---|---|---|---|---|
| | A549 | SK-OV-3 | SK-MEL-2 | HCT15 |
| 0.0001 | 93.23 | 94.45 | 94.45 | 102.34 |
| 0.001 | 97.98 | 100.12 | 93.83 | 105.63 |
| 0.01 | 102.62 | 99.81 | 99.46 | 107.01 |
| 0.1 | 102.22 | 102.80 | 103.86 | 105.29 |
| 1.0 | 101.45 | 102.54 | 102.59 | 86.63 |
| 10.0 | 98.84 | 96.28 | 97.30 | 86.27 |
| $IC_{50}$ | >10.0 | >10.0 | >10.0 | >10.0 |

TABLE 4

Anticancer activity of compound 3

| Concentration (mM) | Cell | | | |
|---|---|---|---|---|
| | A549 | SK-OV-3 | SK-MEL-2 | HCT15 |
| 0.0001 | 95.36 | 98.81 | 99.03 | 101.22 |
| 0.001 | 99.30 | 98.43 | 104.42 | 106.07 |
| 0.01 | 94.81 | 102.58 | 97.76 | 105.35 |
| 0.1 | 91.26 | 100.26 | 102.99 | 107.55 |
| 1.0 | 100.21 | 98.79 | 101.04 | 106.20 |
| 10.0 | 68.29 | 18.74 | 87.55 | 11.54 |
| $IC_{50}$ | >10.0 | 4.52 | >10.0 | 3.74 |

TABLE 5

Anticancer activity of compound 4

| Concentration (mM) | Cell | | | |
|---|---|---|---|---|
| | A549 | SK-OV-3 | SK-MEL-2 | HCT15 |
| 0.0001 | −22.72 | −82.51 | −54.78 | −65.65 |
| 0.001 | −16.42 | −81.43 | −56.49 | −52.68 |
| 0.01 | −10.11 | −90.31 | −65.28 | −65.82 |
| 0.1 | −56.45 | −90.85 | −80.17 | −71.83 |
| 1.0 | −34.39 | −45.23 | −59.12 | −67.64 |
| 10.0 | −64.60 | −36.49 | −32.08 | −49.09 |
| $IC_{50}$ | <0.0001 | <0.0001 | <0.0001 | <0.0001 |

TABLE 6

Anticancer activity of compound 5

| Concentration (mM) | Cell | | | |
|---|---|---|---|---|
| | A549 | SK-OV-3 | SK-MEL-2 | HCT15 |
| 0.0001 | 98.46 | 102.85 | 92.12 | 102.08 |
| 0.001 | 98.27 | 97.87 | 92.10 | 105.12 |
| 0.01 | 97.65 | 105.06 | 101.18 | 102.77 |
| 0.1 | 99.81 | 104.50 | 104.75 | 105.17 |
| 1.0 | 99.22 | 101.23 | 103.54 | 103.82 |
| 10.0 | 10.35 | 2.60 | 17.51 | −63.17 |
| $IC_{50}$ | 3.74 | 3.21 | 4.22 | 1.93 |

TABLE 7

Anticancer activity of compound 6

| Concentration (mM) | Cell | | | |
|---|---|---|---|---|
| | A549 | SK-OV-3 | SK-MEL-2 | HCT15 |
| 0.0001 | 95.03 | 93.93 | 95.53 | 94.66 |
| 0.001 | 31.35 | 11.65 | 74.36 | 16.49 |
| 0.01 | 4.64 | −65.82 | 27.44 | −55.73 |
| 0.1 | 2.86 | −70.93 | −29.72 | −72.72 |
| 1.0 | 4.22 | −63.94 | −61.33 | −75.37 |
| 10.0 | 3.52 | −71.47 | −72.19 | −68.98 |
| $IC_{50}$ | 0.0007 | 0.0004 | 0.0028 | 0.0004 |

TABLE 8

Anticancer activity of compound 7

| Concentration (mM) | Cell | | | |
|---|---|---|---|---|
| | A549 | SK-OV-3 | SK-MEL-2 | HCT15 |
| 0.0001 | 96.62 | 93.40 | 100.12 | 103.20 |
| 0.001 | 101.48 | 96.29 | 106.18 | 103.56 |
| 0.01 | 100.72 | 99.67 | 107.91 | 105.34 |
| 0.1 | 108.40 | 99.82 | 101.40 | 105.40 |
| 1.0 | 101.96 | 102.24 | 105.53 | 102.31 |
| 10.0 | 103.02 | 96.88 | 106.64 | 83.30 |
| $IC_{50}$ | >10.0 | >10.0 | >10.0 | >10.0 |

TABLE 9

Anticancer activity of compound 8

| Concentration (mM) | Cell | | | |
|---|---|---|---|---|
| | A549 | SK-OV-3 | SK-MEL-2 | HCT15 |
| 0.0001 | 91.20 | 87.46 | 96.64 | 102.53 |
| 0.001 | 86.40 | 82.77 | 98.23 | 97.10 |
| 0.01 | 49.33 | 34.41 | 84.56 | 17.31 |
| 0.1 | −11.78 | −63.80 | 36.36 | −68.64 |
| 1.0 | −32.54 | −73.49 | −39.83 | −68.53 |
| 10.0 | −64.23 | −69.86 | −53.70 | −65.16 |
| $IC_{50}$ | 0.009 | 0.007 | 0.076 | 0.004 |

In conclusion, according to the examples of the present disclosure, the trichothecene compounds or mixtures thereof may exhibit different anticancer activities not only against 4 types of human breast cancer cells (Bt549, HCC70, MDA-MB-231, MDA-MB-468) but also against lung cancer, ovarian cancer, skin cancer, and colorectal cancer, and in regard to the cytotoxicity of the individual compounds, all of compounds 1 to 8 exhibited a potent anticancer effect.

According to the examples of the present disclosure, the trichothecene compounds not only exhibit more superior anticancer activity against 4 types of human breast cancer cells than doxorubicin and etoposide, which are commonly used as anticancer agents in clinical trials, but also have excellent anticancer activity against lung cancer, ovarian cancer, skin cancer, and colorectal cancer, and thus are expected to be effective used as an anticancer agent.

As is apparent from the foregoing description, novel compounds of the present disclosure exhibit an excellent activity of inhibiting the proliferation of various cancer cells, such as breast cancer cells, lung cancer cells, ovarian cancer cells, skin cancer cells, and colorectal cancer cells, and thus can be effectively used for preventing, alleviating, or treating cancer.

The foregoing description of the present disclosure is provided only for illustrative purposes, and it will be understood by those of ordinary skill in the art to which the present disclosure pertains that the invention may be easily modified into many different forms without departing from the technical spirit or essential characteristics thereof. Thus, the embodiments described herein should be considered in an illustrative sense only and not for the purpose of limitation.

What is claimed is:

1. A compound having a structural formula selected from the group consisting of the following structural formulae 1 to 3:

[Structural formula 1]

($R_1$ is one selected from the group consisting of OH, and $R_2$ is one selected from the group consisting of OH, and

[Structural formula 2]

($R_1$ and $R_2$ are each independently one selected from the group consisting of OH, and

[Structural formula 3]

2. The compound of claim 1, wherein the compound is isolated from *Podostroma cornu-damae* or a culture thereof.

3. The compound of claim 1, wherein the compound is selected from the group consisting of the following compounds 1 to 8:

Compound 1: (1R,4Z,6E,8R,12E,16aR,19S,20S,20aR, 22R,23S,23aS)-19,23-dihydroxy-8-((R)-1-hydroxyethyl)-12,19,23a-trimethyl-10,11,17,18,19,20,20a,22, 23,23a-decahydro-1H-1,22:20,23-dimethano[1,6,12] trioxacyclooctadecino[3,4-d]chromene-3,14(8H,16H)-dione;

Compound 2: (2E,4E,6R,7R)-methyl-7-hydroxy-6-(((E)-5-(((2R,2'S,4R,5S,5aR,9aR)-4-hydroxy-5,8-dimethyl-2,3,4,5,5a,6,7,9a-octahydrospiro[2,5-methanobenzo[b] oxepine-10,2'-oxiran]-5a-yl)methoxy)-3-methyl-5-oxopent-3-en-1-yl)oxy)octa-2,4-dienoate;

Compound 3: (E)-2-((3S)-3-hydroxy-2-((S)-1-hydroxyethyl)-2-((1 E,3Z)-5-(((2R,2'S,4R,5S,5aR,9aR)-5a-(hydroxymethyl)-5,8-dimethyl-2,3,4,5,5a,6,7,9a-octahydrospiro[2,5-methanobenzo[b]oxepine-10,2'-oxiran]-4-yl)oxy)-5-oxopenta-1,3-dien-1-yl)dihydro-2H-pyran-4(3H)-ylidene)acetic acid;

Compound 4: (1R,2'S,4Z,6E,8R,12E,16aR,20aR,22R, 23aS)-8-((R)-1-hydroxyethyl)-12,19,23a-trimethyl-1, 10,11,17,18,20a,22,23a-octahydrospiro[1,22-methano [1,6,12]trioxacyclooctadecino[3,4-d]chromene-23,2'-oxirane]-3,14(8H,16H)-dione;

Compound 5: (2'S,4E,9R,10E,12Z,16R,16aS,18R,19aR, 23aR,25R)-6,7,16,16a,19a,22-Hexahydro-25-hydroxy-9-[(1 S)-1-hydroxyethyl]-16a,21-dimethylspiro[5,9:16, 18-dimethano-1H,3H,23H-[1,6,12] trioxacyclooctadecino[3,4-d][1]benzopyran-17(18H), 2'-oxirane]-3,14(9H)-dione;

Compound 6: Epi-(2'S,4E,9R,10E,12Z,16R,16aS,18R, 19aR,23aR,25R)-6,7,16,16a,19a,22-Hexahydro-25-hydroxy-9-[(1 S)-1-hydroxyethyl]-16a,21-dimethylspiro [5,9:16,18-dimethano-1H,3H,23H-[1,6,12] trioxacyclooctadecino[3,4-d][1]benzopyran-17(18H), 2'-oxirane]-3,14(9H)-dione;

Compound 7: (2Z,4E)-(2R,2'S,4R,5S,5aR,9aR)-5a-(hydroxymethyl)-5,8-dimethyl-2,3,4,5,5a,6,7,9a-octahydrospiro[2,5-methanobenzo[b]oxepine-10,2'-oxiran]-4-yl 7-hydroxy-6-(2-(5-oxo-2,5-dihydrofuran-3-yl) ethoxy)octa-2,4-dienoate; and

Compound 8: (2Z,4E)-(2R,2'S,4R,5S,5aR,9aR)-5a-((((E)-5-hydroxy-3-methylpent-2-enoyl)oxy)methyl)-5,8-dimethyl-2,3,4,5,5a,6,7,9a-octahydrospiro[2,5-methanobenzo[b]oxepine-10,2'-oxiran]-4-yl-7-hydroxy-6-(2-(5-oxo-2,5-dihydrofuran-3-yl)ethoxy) octa-2,4-dienoate.

4. A composition comprising, as an active ingredient, a compound having a structural formula selected from the group consisting of the following structural formulae 1 to 3 or a pharmacologically acceptable salt thereof:

[Structural formula 1]

($R_1$ is one selected from the group consisting of OH, and $R_2$ is one selected from the group consisting of OH, and

[Structural formula 2]

($R_1$ and $R_2$ are each independently one selected from the group consisting of OH, , and

.)

[Structural formula 3]

5. The composition of claim 4, wherein the composition is a pharmaceutical composition or a food composition.

6. A method of treating cancer, the method comprising administering, to an individual, a composition comprising, as an active ingredient, a compound having a structural formula selected from the group consisting of the following structural formulae 1 to 3 or a pharmacologically acceptable salt thereof:

[Structural formula 1]

($R_1$ is one selected from the group consisting of OH, and
R₂ is one selected from the group consisting of OH, and

.)

[Structural formula 2]

(R₁ and R₂ are each independently one selected from the group consisting of OH, -continued , and

,)

[Structural formula 3]

wherein the cancer comprises one or more selected from the group consisting of lung cancer, colorectal cancer, skin cancer, ovarian cancer, and breast cancer.

7. The method of claim 6, wherein the composition is a pharmaceutical composition or a food composition.

* * * * *